United States Patent
Abe et al.

(10) Patent No.: US 11,478,009 B2
(45) Date of Patent: Oct. 25, 2022

(54) FOOD COMPOSITION

(71) Applicant: OTSUKA PHARMACEUTICAL FACTORY, INC., Naruto (JP)

(72) Inventors: Kazumi Abe, Naruto (JP); Naoto Ishibashi, Naruto (JP)

(73) Assignee: OTSUKA PHARMACEUTICAL FACTORY, INC., Tokushima (JP)

( * ) Notice: Subject to any disclaimer, the term of this patent is extended or adjusted under 35 U.S.C. 154(b) by 921 days.

(21) Appl. No.: 15/021,357

(22) PCT Filed: Jun. 12, 2014

(86) PCT No.: PCT/JP2014/065655
§ 371 (c)(1),
(2) Date: Mar. 11, 2016

(87) PCT Pub. No.: WO2015/037294
PCT Pub. Date: Mar. 19, 2015

(65) Prior Publication Data
US 2016/0227822 A1    Aug. 11, 2016

(30) Foreign Application Priority Data

Sep. 13, 2013  (JP) .............................. JP2013-190536

(51) Int. Cl.
*A23L 33/00* (2016.01)
*A23L 33/20* (2016.01)
*A23L 29/212* (2016.01)
*A23L 29/256* (2016.01)
*A23L 29/269* (2016.01)

(52) U.S. Cl.
CPC ............. *A23L 33/40* (2016.08); *A23L 29/212* (2016.08); *A23L 29/256* (2016.08); *A23L 29/272* (2016.08); *A23L 33/20* (2016.08); *A23V 2002/00* (2013.01)

(58) Field of Classification Search
CPC .......... A23V 2002/00; A23V 2200/228; A23V 2200/30; A23V 2250/5036; A23V 2250/5054; A23V 2250/5118; A23L 29/212; A23L 29/256; A23L 29/272; A23L 33/20; A23L 33/407; A23L 33/40
See application file for complete search history.

(56) References Cited

U.S. PATENT DOCUMENTS

| | | | | | |
|---|---|---|---|---|---|
| 4,965,080 A | * | 10/1990 | Akasaka | .............. | A23C 20/025 426/104 |
| 5,368,871 A | * | 11/1994 | Konstance | ................ | A23J 3/08 426/104 |
| 6,458,395 B1 | | 10/2002 | Emoto | | |

FOREIGN PATENT DOCUMENTS

| CN | 101102681 A | 1/2008 |
|---|---|---|
| JP | 63-14667 A | 1/1988 |
| JP | 63-14668 A | 1/1988 |
| JP | 11-75769 A | 3/1999 |
| JP | 2004-147639 A | 5/2004 |
| JP | 2009-278968 A | 12/2009 |
| JP | 2011-105702 A | 6/2011 |
| JP | 2011-167142 A | 9/2011 |
| KR | 10-2012-0047250 A | 5/2012 |
| WO | 2006/054886 A1 | 5/2006 |
| WO | 2013/073303 A1 | 5/2013 |

OTHER PUBLICATIONS

Office Action dated Mar. 13, 2018, issued in Japanese Patent Application No. 2015-536462, with translation.
European Search Report dated Feb. 14, 2017, issued in counterpart application No. EP14844063.9.
European Search Report dated 14844063.9, issued in counterpart application No. 14844063.9.
International Search Report dated Sep. 9, 2014, issued in counterpart International Application No. PCT/JP2014/065655 (1 page).
Kanaya et al., "125 Dysphagia Recipes Based on Dysphagia Food Pyramid", Ishiyaku Pub., Inc., First Edition, Sep. 15, 2007, cited in the Specification, w/ English machine translation (7 pages).
Office Action dated Apr. 2, 2019, issued in counterpart CN Application No. 201480050408.8, with English translation. (15 pages).
Office Action dated Dec. 21, 2020, issued in counterpart KR Application No. 10-2016-7009350, with English Translation. (12 pages).

* cited by examiner

*Primary Examiner* — Jyoti Chawla
(74) *Attorney, Agent, or Firm* — WHDA, LLP

(57) ABSTRACT

The present invention provides a food composition that makes it possible to effectively conduct mastication and swallowing training. The food composition contains a starch, a gelling agent, a paste, and water, the amount of the water contained in the composition being 65 wt % or more and less than 90 wt %, the total amount of the starch, the gelling agent, the paste, and the water being 85 to 100 wt %, the composition having a fracture stress of 20,000 to 70,000 $N/m^2$.

14 Claims, No Drawings

FOOD COMPOSITION

TECHNICAL FIELD

The present invention relates to a food composition.

BACKGROUND ART

Mastication and swallowing dysfunction, which is also called eating and swallowing disorder, refers to a disorder in a series of eating actions, i.e., recognizing food, putting it into the mouth, and sending it to the stomach. Mastication and swallowing dysfunction can occur as a result of a disease or aging, and is increasing, in particular, with the advent of aging societies. For example, a 2005 patient survey reported that 24.3% of the total estimated number of patients, such as those in long-term medical care, required monitoring when swallowing, while 25.9% were not capable of swallowing. When patients lapse into mastication and swallowing dysfunction, malnutrition, dehydration, pneumonia or suffocation due to aspiration, or the like may possibly occur. Moreover, when patients lapse into this dysfunction, the pleasure of consuming food orally is lost, possibly deteriorating the patients' quality of life. For this reason, training has been conducted to improve mastication and swallowing dysfunction as much as possible to restore the functions thereof.

The training for improving or restoring mastication or swallowing functions is roughly categorized into indirect (basic) training and direct (ingestion) training. Food is not provided in indirect training, which is conducted by stimulating or moving organs that are involved in ingestion, masticating, and swallowing to improve the functions thereof. Food is actually provided in direct training, which is conducted while devising the type and shape of the food according to the severity of mastication or swallowing disorders, and gradually bringing the food closer to regular diet in stages. Direct training has recently begun using various forms of meals (e.g., slurry, jelly, mousse, paste, bite-sized, and shaped). When focusing on "swallowing," for example, meals in the form of slurry, jelly, mousse, paste, or the like are used. Training for "mastication and swallowing," rather than only swallowing, also uses bite-sized meals, shaped meals, and the like.

According to, for example, the "dysphagia food pyramid" shown in Non-patent Literature (NPL) 1, foods are divided into six steps corresponding to levels 0 to 5, based on the severity of the mastication and swallowing disorder: level 0 comprises initiation diets; levels 1 to 3 comprise swallowing diets; level 4 comprises transition diets (nursing diets); and level 5 comprises regular diets (FIG. 1). According to the "dysphagia food pyramid," the diets of levels 0 to 3 focus on "swallowing," and the diets of level 4 also take "mastication" into consideration.

The transition from "command swallowing" training to "mastication and swallowing" training adds the movement of "mastication." It has been clarified that the faucial area is open during the mastication movement, and a bolus of food is sent near the pharynx during mastication. In view of this, there is presumably a risk of aspiration during mastication, and caution is particularly required when the stage is upgraded, i.e., when diets for swallowing training for people who are capable of command swallow are upgraded to diets for mastication training in irregular forms, additionally containing bite-sized and shaped foods (equivalent to a case in which the stage transitions from level 3 to level 4 in the "dysphagia food pyramid").

For this reason, the development of a composition for mastication and swallowing training that makes it possible to safely conduct direct training, and that provides reduced risk of aspiration, has been demanded. For example, a banana may sometimes be used in direct mastication training. As the initial hardness, a banana has a fracture stress of about 40,000 N/m$^2$, and after being masticated in a usual manner (e.g., after 5 mastications), the fracture stress becomes about 1,000 N/m$^2$. Depending on the variety of the banana and its degree of ripening, syneresis occurs when the banana is masticated, creating the risk of aspiration. Easily masticated foods and/or easily swallowed foods are in wide development, and some products have been placed on the market. As an example of a composition that provides reduced risk of aspiration and that is useful in direct training, a composition that contains edible oil and a gelatinous material and that is used by adding it to food has been reported (Patent Literature (PTL) 1). Even though such products and compositions have already been reported, means useful for mastication and swallowing training are still in demand.

CITATION LIST

Patent Literature

PTL 1: JP2011-105702A

Non-Patent Literature

NPL 1: Setsuko Kanaya et al., "*Engesyoku pyramid ni yoru engesyoku recipe 125*" [125 dysphagia recipes based on dysphagia diets pyramid], Fumie Egashira et al. ed., Ishiyaku Publishers, Inc., September, 2007, FIG. 1

SUMMARY OF INVENTION

Technical Problem

An object of the present invention is to provide a food composition. In particular, an object of the present invention is to provide a food composition that is suitable for mastication and swallowing training, and that makes it possible to effectively conduct mastication and swallowing training. Further, in particular, an object of the present invention is to provide a composition that is suitable for mastication and swallowing training, and that makes it possible to safely and effectively conduct mastication and swallowing training while reducing aspiration risk, even when the subject is a person who can swallow whole but still has difficulty in swallowing after mastication.

Solution to Problem

To train people having mastication and swallowing difficulties to improve the functions thereof, as stated above, a composition for mastication and swallowing must have a certain degree of hardness to facilitate mastication. At the same time, to reduce the risk of aspiration (in particular, aspiration at the time of mastication) in people having mastication and swallowing difficulties, the composition must be soft enough to be swallowed whole. However, a composition that becomes overly soft when masticated is not suitable for mastication training.

To achieve the above objects, the present inventors conducted extensive research, and found that a composition having the following characteristics makes it possible to conduct effective mastication and swallowing training while reducing aspiration risk, i.e., a composition containing a starch, a gelling agent, a paste, and water, the water content in the composition being 65 wt % or more and less than 90 wt %, the total amount of the starch, the gelling agent, the paste, and the water in the composition being 85 to 100 wt %, and the composition having a fracture stress of 20,000 to 70,000 N/m². The present inventors conducted further research based on such findings. The present invention has thus been accomplished.

More specifically, the present invention provides the following invention.

Item 1: A food composition containing a starch, a gelling agent, a paste, and water, the amount of the water contained in the composition being 65 wt % or more and less than 90 wt %, the total amount of the starch, the gelling agent, the paste, and the water being 85 to 100 wt %, the composition having a fracture stress of 20,000 to 70,000 N/m².

Item 2. The food composition according to Item 1, wherein the composition has an adhesiveness of 4,000 J/m³ or less.

Item 3. The food composition according to Item 1 or 2, wherein the composition contains the starch in an amount of 5 to 10 wt %.

Item 4. The food composition according to any one of Items 1 to 3, wherein the composition contains the gelling agent in an amount of 0.5 to 3 wt %.

Item 5. The food composition according to any one of Items 1 to 4, wherein the composition contains the paste in an amount of 5 to 20 wt %.

Item 6. The food composition according to any one of Items 1 to 5, wherein the syneresis rate is 0 to 3%.

Item 7. The food composition according to any one of Items 1 to 6, wherein the total amount of the starch and the gelling agent is about 1 or more by weight, based on the amount of the paste.

Item 8. The food composition according to any one of Items 1 to 7, wherein the paste is at least one member selected from the group consisting of plant pastes and pastes made from animal-derived materials.

Item 9. The food composition according to any one of Items 1 to 8, wherein the paste contains an oil.

Item 10. The food composition according to any one of Items 1 to 9, wherein the paste is made from at least one plant selected from the group consisting of seeds and fruits.

Item 11. The food composition according to any one of Items 1 to 10, wherein the paste is a sesame paste.

Item 12. The food composition according to any one of Items 1 to 11, wherein the gelling agent is at least one member selected from the group consisting of κ carrageenan and gellan gum.

Item 13. The food composition according to any one of Items 1 to 12, wherein the composition has a fracture stress of 1,000 to 5,000 N/m² after 20 mastications.

Item 14. The food composition according to any one of Items 1 to 13, wherein the composition has a fracture stress of 1,000 to 10,000 N/m² after 5 mastications.

Item 15. The food composition according to any one of Items 1 to 14, wherein the composition has an adhesiveness of 500 J/m³ or less after 20 mastications.

Item 16. The food composition according to any one of Items 1 to 15, wherein the composition has an adhesiveness of 1,000 J/m³ or less after 5 mastications.

Item 17. The food composition according to any one of Items 1 to 16, wherein the composition has a cohesiveness of 0.4 to 0.8.

Item 18. The food composition according to any one of Items 1 to 17, wherein the composition has a cohesiveness of 0.4 to 0.8 after 20 mastications.

Item 19. The food composition according to any one of Items 1 to 18, wherein the composition has a cohesiveness of 0.4 to 0.8 after 5 mastications.

Item 20. The food composition according to any one of Items 1 to 19, wherein the composition is retort-sterilized.

Item 21. The food composition according to any one of Items 1 to 20, for use in mastication and swallowing training.

Advantageous Effects of Invention

The food composition according to the present invention makes it possible to effectively conduct mastication and swallowing training. In particular, the food composition of the present invention has a hardness that is sufficient to facilitate mastication, and achieves reduced syneresis; thus, when this composition is supplied to the oral cavity, more effective mastication training can be conducted while providing a reduced risk of aspiration of a bolus, a liquid, and the like, that are separated from the composition during mastication. Therefore, the food composition of the present invention is suitable for mastication training. In addition, the food composition of the present invention is not only easily swallowed, but also provides improved safety in swallowing training.

As described above, the food composition according to the present invention makes it possible to effectively and safely conduct mastication and swallowing training while reducing risk of aspiration. The food composition of the present invention may be of any shape and size, and may have any flavor; it is thus possible for the composition to meet the various preferences of trainers.

DESCRIPTION OF EMBODIMENTS

The food composition of the present invention contains a starch, a gelling agent, a paste, and water. The amount of the water contained in the composition is 65 wt % or more and less than 90 wt %, and the total amount of the starch, the gelling agent, the paste, and the water in the composition is 85 to 100 wt %. The composition has a fracture stress of 20,000 to 70,000 N/m².

The following describes the present invention in more detail.

The starch is not limited as long as it is edible, and any starch may be used. Examples of starch include starches derived from natural products (hereinafter referred to as native starch), including starches derived from plants, such as corn, potato, sweet potato, tapioca, bracken, wheat, rice, rye, foxtail millet, Japanese millet, adlay, mung beans, adzuki beans, soybeans, buckwheat noodles, kudzu, sago, and waxy corn; and modified starches in which native starches are, for example, physically, chemically, and/or enzymatically treated. Examples of modified starches include derivatives, decomposition products, pregelatinized products, and the like, of starches derived from natural products. More specific examples include acetylpropyl distarch phosphate and like acetylated distarch phosphate, acetylated distarch adipate, acetylated oxidized starch, starch sodium octenyl succinate, starch acetate, oxidized starch, hydroxypropyl starch, hydroxypropyl distarch phosphate, phosphated distarch phosphate, monostarch phosphate, and distarch phosphate. As a starch, for example, modified starches are preferable, crosslinked modified starches (crosslinked starches) are more preferable, highly crosslinked starches are furthermore preferable, and highly crosslinked starches in which substantially no breakdown is observed in a Brabender amylogram are particularly preferable. Preferable embodiments include an example that uses acetylated distarch phosphate, such as acetylpropyl distarch phosphate.

These starches may be used singly, or in a combination of two or more.

The amount of the starch contained is not limited as long as the effect of the present invention is obtained. The starch is contained in the food composition in an amount of, for example, 5 to 10 wt %, preferably 6 to 9 wt %, and more preferably 7 to 8 wt %. The amount of the starch contained affects the variation of the hardness. If the amount is less than 5 wt %, the cohesiveness tends to worsen during mastication training, and if the amount is more than 10 wt %, the composition tends to liquefy, increasing the risk of aspiration.

The gelling agent is not limited as long as it is edible, and any gelling agents may be used. Examples of gelling agents include carrageenans (κ, ι, and λ types), sodium carboxymethyl cellulose, tara gum, gellan gum, sodium alginate, potassium alginate, alginic acid ester, guar gum, gum arabic, gum tragacanth, karaya gum, pectin, xanthan gum, curdlan, pullulan, gelatin, agar, locust bean gum, galactomannan, glucomannan, tamarind seed gum, psyllium seed gum, gum ghatti, arabinogalactan, kelp acid, soybean protein, crystalline cellulose, and the like.

Preferable examples of gelling agents include carrageenans, agar, sodium alginate, gellan gum, xanthan gum, sodium carboxymethyl cellulose, guar gum, soybean protein, and crystalline cellulose. More preferable examples of gelling agents include κ carrageenan, xanthan gum, and gellan gum, and furthermore preferable examples of gelling agents include κ carrageenan and gellan gum. For example, when a starch with a lower degree of crosslinking is used from among the starches mentioned above, it is preferable to use a gelling agent that can easily impart strength to the resulting composition, from the viewpoint of effectively achieving the effect of the present invention. It is also preferable to use a gelling agent that can easily impart strength, elasticity, and/or stability to the composition, from the viewpoint of effectively achieving the effect of the present invention. In the present invention, the gelling agent is substantially starch-free.

These gelling agents may be used singly, or in a combination of two or more.

The amount of the gelling agent contained is not limited as long as the effect of the present invention is obtained. The proportion of the gelling agent in the food composition is, for example, 0.5 to 3 wt %, preferably 0.7 to 1.5 wt %, and more preferably 0.9 to 1.1 wt %. The amount of the gelling agent contained affects the hardness in mastication. If the amount is less than 0.5 wt %, the composition tends to become overly soft, and cannot achieve a hardness suitable for mastication. If the amount is more than 3 wt %, the composition tends to fail to achieve a hardness at which chewing can be performed, even if the number of mastications is increased. A preferable amount of the gelling agent may be appropriately set by a person skilled in the art according to the type of the starch.

The paste is not limited as long as it is edible, and any paste may be used. To this end, the paste of the present invention is not limited, and may be, for example, plant pastes and pastes made from animal-derived materials. The paste may contain an oil. Oil as used herein refers to those in a solid or liquid form at ordinary temperature. Examples of preferable pastes include an oil-containing paste. To this end, the oil-containing paste is not limited. Examples thereof include oil-containing plant pastes, oil-containing pastes made from animal-derived materials, and the like.

Although not intended to limit the invention, the following describes in more detail an example regarding plant pastes. Specifically, the parts of plants contained in the paste are not limited as long as the effect of the present invention is obtained, and may be, for example, seeds, fruits, flowers, stems, roots, leaves, and the plant in its entirety; and preferably, for example, plant seeds and fruits. Examples of the plants include sesame, peanuts, almonds, cashew nuts, soybeans, adzuki beans, cacao beans, coffee beans, pumpkins, sweet potatoes, tomatoes, and the like. Preferable examples of the plants include sesame, peanuts, almonds, adzuki beans, cacao beans, pumpkins, sweet potatoes, and the like. More preferable examples of the plants include sesame, peanuts, cacao beans, and the like. These plants may be directly used to prepare a paste. Alternatively, these plants may be used to prepare a paste after being subjected to desired steps, such as concentration; mixing by stirring; drying; heating; and emulsification. Although not intended to limit the invention, the following describes in more detail examples regarding pastes made from animal-derived materials. Specifically, examples of the animal-derived materials include milk, butter, cheese, and the like. These materials may be used directly to prepare a paste. Alternatively, these materials may be used to prepare a paste after being subjected to desired steps, such as concentration; mixing by stirring; drying; heating; and emulsification.

Examples of the paste include a sesame paste, a peanut paste, an almond paste, a cashew nut paste, a soybean paste (including, for example, soybean flour paste), an adzuki bean paste, a cacao bean paste, a chocolate paste, a coffee bean paste, a pumpkin paste, a sweet potato paste, condensed milk, a milk cream paste, white sauce, plant-based fresh cream, dairy fresh cream, and the like. Preferable examples include a sesame paste, a peanut paste, a chocolate paste, condensed milk, a milk cream paste, white sauce, plant-based fresh cream, dairy fresh cream, and the like.

Of these pastes, a more preferable paste is a paste containing an oil, carbohydrate, and protein, and a furthermore preferable paste is an emulsified paste in which an oil, carbohydrate, and protein are combined without being separated. An oil, carbohydrate, and protein may be those inherent in the plants or animal-derived materials mentioned above. Otherwise, they may be arbitrarily incorporated as required, as described below. The paste may be prepared by pasting the starting materials, such as plants and animal-derived materials, by using a known method (e.g., grinding or concentrating), according to the starting materials to be used. The paste may be made from only plants or animal-derived materials. It is also possible to use a paste prepared by combining plants or animal-derived materials, and optional components, such as an oil, carbohydrate, protein, a thickener, a stabilizer, and an anti-oxidant, as required. Alternatively, it is also possible to use a commercially available paste. Preferable examples of such a paste include a sesame paste with 5% or less of water, and an alkaline or neutral oil-containing paste.

Various starting materials, such as the plants, the parts of a plant, and the animal-derived materials may be used alone, or in a combination of two or more. Further, the pastes may be used alone, or in a combination of two or more.

The amount of the paste contained is not limited as long as the effect of the present invention is obtained. The proportion of the paste in the food composition is, for example, 5 to 20 wt %, preferably 5 to 10 wt %, and more preferably 7 to 9 wt %. If the amount of the paste is less than 5 wt %, syneresis tends to easily occur, and if the amount is more than 20 wt %, the composition tends to become sticky.

The water mentioned above is not limited, and may be distilled water, ion-exchanged water, purified water, ultrapure water, and the like. The amount of the water contained is not limited as long as the effect of the present invention is obtained. The proportion of the water in the food composition is, for example, 65 wt % or more and less than 90 wt %, and preferably 70 to 85 wt %. In this specification, the amount of the water does not include the amount of water contained in the paste.

In addition to the components above, the food composition of the present invention may optionally contain any components, such as oils, saccharides, salts, soy sauce, miso, dashi soy sauce, various extracts, various spices, acidulants, amino acids, minerals, vitamins, flavors, colors, anti-oxidants, nutrition enhancers, and the like, as long as the effect of the present invention is not impaired. These are suitably selected according to the purpose of imparting, for example, the taste, aroma, color, or desired functions to the food composition, and the amount of each component contained in the food composition is also suitably set according to the purpose.

The total amount of the starch and the gelling agent by weight based on the amount of the paste is not limited as long as the effect of the present invention is obtained, and may be suitably set by a person skilled in the art. As a preferable example, the total amount of the starch and the gelling agent by weight is about 1 or more, more preferably about 1 to 2.2, furthermore preferably about 1 to 1.2, and particularly preferably about 1 to 1.1, based on the amount of the paste.

Although it is not limited as long as the effect of the present invention is obtained, and preferably from the viewpoint of the food composition being used by people having difficulties in taking ordinary meals, the food composition of the present invention more preferably contains a protein in an amount of, for example, about 1.5 to 5 wt %; a lipid in an amount of, for example, about 4 to 8 wt %; and a carbohydrate of, for example, about 9 to 30 wt %.

The food composition of the present invention has a hardness at the time of use (initial stage) of 20,000 to 70,000 $N/m^2$, and preferably 25,000 to 42,000 $N/m^2$, in terms of the fracture stress. This hardness facilitates mastication, and also makes it possible to conduct effective mastication and swallowing training. Therefore, the food composition of the present invention is suitable for mastication training, and further for mastication and swallowing training.

The food composition of the present invention preferably has hardness within a certain range even after several mastications. From this viewpoint, the fracture stress after, for example, 5 mastications is preferably 1,000 to 10,000 $N/m^2$, and more preferably 2,500 to 10,000 $N/m^2$. The food composition of the present invention preferably has a hardness within a certain range, even when mastication is further continued. From this viewpoint, the fracture stress after 20 mastications is preferably 1,000 to 5,000 $N/m^2$, and more preferably 1,200 to 5,000 $N/m^2$. As such, when the food composition of the present invention has a hardness within a certain range even after, for example, 5 mastications, and further 20 mastications, the composition soon achieves a moderate hardness as a result of, in particular, the mutual reaction of the saccharides and saliva in the oral cavity. Specifically, after several (e.g., 5) mastications, the composition is immediately softened, and therefore becomes easy to swallow. Nevertheless, the composition does not become overly soft after being masticated over the usual number of mastication times (e.g., 20 times); therefore, the composition is highly suitable for mastication training, and further for mastication and swallowing training.

Further, the food composition of the present invention preferably has an adhesiveness at the initial stage of, for example, 4,000 $J/m^3$ or less, from the viewpoint of the adherence and stickiness of the composition in the oral cavity and the pharynx. The food composition of the present invention preferably has a certain degree of adhesiveness even after being masticated. The adhesiveness obtained immediately after being masticated is preferably 1,500 $J/m^3$ or less, and more preferably 500 $J/m^3$. More specifically, the adhesiveness of the food composition of the present invention after, for example, 5 mastications is preferably 1,000 $J/m^3$ or less. Additionally, the adhesiveness of the food composition of the present invention is preferably within a certain degree even when mastication is further continued. From this viewpoint, the adhesiveness after, for example, 20 mastications is preferably 500 $J/m^3$ or less. As such, when the food composition of the present invention has a certain adhesiveness at the initial stage as mentioned above, or when the food composition of the present invention has a certain adhesiveness as mentioned above even after, for example, 5 mastications, and further 20 mastications, the composition soon achieves a moderate adhesiveness as a result of, in particular, the mutual reaction of the saccharides and saliva in the oral cavity, and the adherence and stickiness of the composition in the oral cavity and the pharynx is further reduced. Therefore, the composition is highly suitable for mastication training, and further for mastication and swallowing training. Moreover, composition remaining in the oral cavity and the pharynx, as well as the risk of aspiration, is also further reduced.

The food composition of the present invention preferably has a cohesiveness at the time of use of 0.4 to 0.8, and more preferably 0.4 to 0.6. The food composition of the present invention preferably has a cohesiveness that is within a certain range even after being masticated. The cohesiveness after, for example, 5 mastications is preferably 0.4 to 0.8, and more preferably 0.4 to 0.6. Further, the food composition of the present invention preferably has a hardness within a certain range even when mastication is further continued, and the cohesiveness after, for example, 20 mastications is preferably 0.4 to 0.8, and more preferably 0.4 to 0.6. As such, when the food composition of the present invention has a cohesiveness within the range above at the initial stage, or when the food composition of the present invention has a certain degree of cohesiveness even after 5 mastications and further 20 mastications, the composition achieves a moderate cohesiveness, in particular, before and after being masticated, and the composition more easily coheres, forming a bolus of food; therefore, the composition has a property of being masticated and swallowed in a satisfactory manner. Accordingly, the composition is highly suitable for mastication training, and further for mastication and swallowing training. Further, the composition is easily swallowed, and composition remaining in the oral cavity and the pharynx, as well as the risk of aspiration, are also further reduced.

In the present invention, the fracture stress, adhesiveness, and cohesiveness are measured using a creep meter. The measurement is performed in accordance with the method disclosed in "Notice No. 0212001 of the Pharmaceutical and Food Safety Bureau" (Feb. 12, 2009), "Permission of Labeling for Food for Special Dietary Uses." Specifically, an excerpt states that a sample is placed in a container having a diameter of 40 mm and a height of 20 mm (if the sample cannot overflow, then the height of the container may be 15 mm); thereafter, the container is filled to a height of 15 mm with the sample, and compression measurement is performed twice using an apparatus that is capable of measuring the compressive stress of the substance by linear motion using a resin plunger having a diameter of 20 mm and a height of 8 mm, at a compression speed of 10 mm/sec with a clearance of 5 mm. The measurement is performed in accordance with this method. More specifically, the measurement is performed in accordance with, for example, the Examples described later.

In terms of the food composition of the present invention, the syneresis rate at the time of use is preferably 0 to 3%, and more preferably 0 to 1%. The syneresis rate is still more preferably substantially 0%. In this manner, when the syneresis rate of the food composition of the present invention is within the above range, the composition has a property of being satisfactorily masticated and swallowed, and is highly suitable for mastication training, and further for mastication and swallowing training. Moreover, the composition is easily swallowed, and composition remaining in the oral cavity and the pharynx, as well as the risk of aspiration, are also further reduced.

In the present invention, the syneresis rate is measured as follows. The following is an example in a case in which the food composition is filled in a container. It is possible for a person skilled in the art to measure the syneresis rate according to the following description.

First, the weight of a food composition is measured at a room temperature (20±2° C.), together with the container (weight (1): food composition weight+container weight). Subsequently, the tare (gauze) weight is measured (weight (2): gauze weight). Kimtowel is placed on a scale, and a gauze is placed thereon to measure the weight (weight (3): gauze weight+kimtowel weight). The food composition removed from the container is placed on the gauze, and the weight is measured (weight (4): the food composition weight+gauze weight+kimtowel weight). The food composition is removed together with the gauze, and the weight is measured (weight (5): syneresis weight+kimtowel weight). The container is tared (weight (6): container weight). The syneresis rate of the food composition is calculated using the following equation: (weight (5)−weight (3)+weight (2))×100/(weight (1)−weight (6)). More specifically, the measurement is performed in accordance with, for example, the Examples described later.

The food composition of the present invention has elasticity at the time of use of preferably 1 to 5, more preferably 1 to 2, and still more preferably 1 to 1.5. The elasticity of the food composition is measured using a creep meter. More specifically, a metal Petri dish having a diameter of 40 mm and a height of 15 mm is filled with the food composition to a height of 15 mm, and the compression measurement is performed once using a cylinder plunger having a diameter of 20 mm at a compression rate of 50%, a compression speed of 1 mm/sec, and at a room temperature (20±2° C.). The elasticity is calculated based on the ratio of the midpoint (absolute distortion: 50%) with respect to the midpoint 1 (absolute distortion: 25%) of the obtained compressive stress curve. The distortion is defined as absolute distortion based on the sample thickness—compression distance. More specifically, the measurement is performed in accordance with, for example, the Examples described later.

The food composition of the present invention is produced by combining a starch, a gelling agent, a paste, and water, and optionally the optional components mentioned above. The production method is not limited as long as the desired effect of the present invention is obtained. To produce the food composition of the present invention, for example, a starch, a gelling agent, a paste, and water, and optionally the optional components mentioned above, are mixed to obtain a uniform dispersion. At this time, to obtain a uniform dispersion without lumps, the paste is preferably mixed after, for example, the starch, gelling agent, and the like are uniformly dispersed. When mixing, water at ordinary temperature (20±10° C.) may be used. It is also possible to use water at a temperature higher than the ordinary temperature as long as it does not reduce the strength of the starch or gelling agent, and a person skilled in the art may suitably determine the water temperature. In the mixing above, a desired apparatus, such as a mixer and a tank, may be used. The size or shape of the blade or the like of a mixer is also not limited. The possible production scale, stirring conditions, and time required for the production are also suitably determined by a person skilled in the art, according to the type etc. of the apparatus used in the production, such as a mixer, a tank, and a blade. In this manner, the food composition of the present invention may be produced. As a more detailed example, the food composition of the present invention may be produced in accordance with the procedures shown in the Examples described below. Further, retort sterilization and the like may be performed, as required.

After each component was mixed as described above, the obtained mixture may be placed in a desired container or the like, as required. The container or the like is not limited, and may be a desired container, such as a pouch, a cup, and a plate with a lid. A container suitable for the purpose may be appropriately determined by a person skilled in the art, in terms of its size, material, shape, and the like. Subsequently, heat (sterilization) treatment may be performed. When the container is resistant to heat, it is possible for the mixture to be subjected to heat (sterilization) treatment while being contained in the container. The heat (sterilization) treatment is also not limited, and may be suitably determined by a person skilled in the art from among boiling, steaming, retort-sterilizing, and the like. When a container that can be hermetically sealed is used, sterilization is preferably performed. The heating temperature, time, etc., may be suitably determined by a person skilled in the art. Retort sterilization may be performed, for example, by a method comprising hermetically sealing the mixture in an airtight opaque container, and performing heat sterilization under pressure. The food composition after retort sterilization may be distributed or stored at ordinary temperature. The temperature and time for the sterilization may be suitably set. For example, the center of the food composition may be heated at 121° C. for 4 minutes under pressure, or the center of the food composition may be heated under pressure by heat conditions equivalent to or more than the heat obtained when heating is performed at 121° C. for 4 minutes under pressure.

The food composition of the present invention may be used for the purpose of, for example, training for only masticating, or training for both masticating and swallowing. The food composition of the present invention may be ingested in combination with general meals in the form of a liquid (including a viscous liquid), puree, mousse, or paste. Specifically, the food composition of the present invention may be ingested in combination with general meals or with meals for swallowing training, as required.

The shape and the size of the food composition of the present invention are not limited as long as the effect of the present invention is obtained. The food composition of the present invention may be of any shape and any size.

Examples of the shape of the food composition of the present invention include a cube, a cuboid, an ellipsoid, a sphere, a triangular pyramid, a quadrangular pyramid, and a sheet. Examples also include a capsule, tablet, and other shapes.

The food composition of the present invention may be of any size, as long as the size can be adjusted to a size usable in training at the time of use. For ease of use, the composition preferably has a size, for example, that can be comfortably placed in the oral cavity. In this case, the composition is sized to have a volume equivalent to that of, for example, 25 mm×25 mm×25 mm at maximum. The composition more preferably is the size of a candy or tablet gum, or a size that is equivalent to the above but has a thickness of 5 mm or more when scooped with a spoon or the like.

When the food composition of the present invention is ingested, mastication and swallowing is facilitated. Further, the food composition of the present invention may be of any shape and size, and may have any flavor; it is thus possible to meet the various preferences of trainers.

Excessive syneresis leads to aspiration. In this respect, the food composition of the present invention has the above composition; therefore, the problem regarding syneresis from this composition is significantly solved, and aspiration due to the internal syneresis (excessive water) exuded from the composition at the time of mastication is significantly reduced. Further, the food composition of the present invention, which has the above composition and initial hardness, reduces aspiration and has an easily chewable hardness. Therefore, the food composition of the present invention is effectively and safely used in mastication training, and is also useful in mastication and swallowing training.

When the food composition of the present invention maintains a certain degree of hardness even after 5 mastications, and further 20 mastications, the composition is immediately softened after several (e.g., 5) mastications, and thus becomes easy to swallow. Nevertheless, the composition does not become overly soft after being masticated over the usual number of mastication times (e.g., 20 times); therefore, the composition is highly suitable for mastication training, and further for mastication and swallowing training. Further, when the food composition of the present invention further has a moderate adhesiveness, the adherence and stickiness of the composition in the oral cavity and the pharynx is further reduced. Therefore, residual composition in the oral cavity and the pharynx, as well as the risk of aspiration, is also further reduced. The composition is thus highly suitable for mastication training, and further for mastication and swallowing training. Additionally, when the food composition of the present invention further has a moderate cohesiveness, the composition has a property of satisfactorily cohering to form a bolus, and is thus excellently masticated and swallowed. Therefore, when the composition further has a moderate cohesiveness, the composition is easily swallowed, and composition remaining in the oral cavity and the pharynx, as well as the risk of aspiration, are also further reduced. The composition is thus highly suitable for mastication training, and further for mastication and swallowing training. Furthermore, when the food composition of the present invention achieves a moderate syneresis rate and/or elasticity, the composition is easily swallowed, and composition remaining in the oral cavity and the pharynx, as well as the risk of aspiration, are also further reduced. The composition is thus highly suitable for mastication training, and further for mastication and swallowing training.

As described above, the food composition of the present invention makes it possible to more effectively and safely conduct mastication training, and further conduct training to improve or restore mastication and swallowing functions while reducing the risk of aspiration. Accordingly, the present invention provides a composition for mastication and swallowing training.

The "composition for mastication and swallowing training" as used herein may be used for the purpose of either one of mastication training or swallowing training, or for the purpose of both mastication training and swallowing training. The "composition for mastication and swallowing training" of the present invention is preferably used for the purpose of training people who can at least swallow whole (who are capable of only swallowing) to masticate and swallow, i.e., for the purpose of training the people to masticate food, send it to the pharynx, and swallow a bolus of food.

EXAMPLES

The following describes in detail the present invention with reference to Examples. However, the present invention is not limited to these Examples.

Example 1: Food Composition

A food composition was produced according to the following procedures.

The following components were used: acetylpropyl distarch phosphate (produced by Shikishima Starch Mfg. Co., Ltd.; degree of crosslinking: high) as a starch; xanthan gum (the viscosity of a 0.3% aqueous solution measured at 20° C. using a B-type viscometer rotor No. 2 (60 rotations) being 150 to 300 mPa·s) and carrageenan (κ type, the jelly strength at 1% (8±1° C., cylinder plunger: 1 cm$^2$, 2 cm/min) being 70 to 140 bloom) as a gelling agent; a sesame paste (in the paste, water content: 2% or less; protein: 14 to 26%; lipid: 58 to 68%; carbohydrate; 6 to 18%; and ash content: 2 to 5%) as an oil-containing plant paste; a crystalline cellulose preparation (crystalline cellulose: guar gum: sodium carboxymethyl cellulose: food material (weight ratio)=20:6.7:6.7:66.6; trade name: San Artist PG, produced by San-Ei Gen F.F.I., Inc.); water; and salt (trade name: edible salt, produced by Otsuka Chemical Co., Ltd.).

The following describes the production procedures: About 600 g of water was placed in a 2-L stainless steel tank, and a TK Unimixer (produced by Tokushu Kika Kogyo Co., Ltd.) was started. A mixture of 85 g of crosslinked starch, 1 g of xanthan gum, 9.83 g of carrageenan, and 5 g of crystalline cellulose preparation was gradually introduced into the stainless-steel tank so as not to form lumps. This operation was performed while the rotation number of the mixer was adjusted to maintain the flow of water. After the mixture was uniformly dispersed, 93 g of sesame paste was gradually introduced thereto to obtain a further uniform dispersion. After dispersion, 1 g of salt was introduced thereto, and the volume was made up to 1,000 g with about 205 g of water, followed by further stirring until a uniform dispersion was obtained. Then, 200 g each of the obtained mixture was placed into a retort pouch to obtain a composition. The thus-obtained composition was subjected to retort sterilization (128° C., 10 minutes, under pressure, F015 or more), and a food composition (Example 1) was thereby obtained. The total amount of the starch and the gelling agent contained in this composition was about 1.1 by weight, based on the amount of the sesame paste. This composition had a fracture stress of 36,900 N/m², and the syneresis rate was 0%.

The fracture stress of the food composition was measured using a creep meter (RE2-33005, produced by Yamaden, Co., Ltd.), as described below. Specifically, the food composition obtained after retort sterilization was placed in a refrigerator at 2 to 6° C. for at least 12 hours, and was then left to stand in a thermostatic room at 20±2° C. for 30 minutes. Thereafter, a metal Petri dish having a diameter of 40 mm and a height of 15 mm was filled with the food composition to a height of 15 mm, and the compression measurement was performed twice using a cylinder plunger having a diameter of 20 mm with a clearance of 5 mm at a compression speed of 10 mm/sec, and at a room temperature (20±2° C.). The fracture stress was calculated based on the obtained texture curve.

The syneresis rate of the food composition was measured at a room temperature (20±2° C.), and calculated in accordance with the following procedures. The weight of the obtained food composition was measured together with the retort pouch (weight 1: food composition weight+retort pouch weight). The tare (gauze) weight was measured (weight 2: gauze weight). Kimtowel was placed on a scale, and a gauze was placed thereon to measure the weight (weight 3: gauze weight+kimtowel weight). The food composition removed from the retort pouch was placed on the gauze, and the weight was measured (weight 4: the food composition weight+gauze weight+kimtowel weight). The food composition was removed together with the gauze, and the weight was measured (weight 5: syneresis weight+kimtowel weight). The tare weight (retort pouch) was measured (weight 6: container weight). The syneresis rate of the food composition was calculated using the following equation: (weight 5−weight 3+weight 2)×100/(weight 1−weight 6).

In the Examples, the adhesiveness and cohesiveness of the food composition were further measured. The adhesiveness and cohesiveness were also measured using the creep meter mentioned above. The food composition that was cooled and left to stand in the thermostatic room as in the fracture stress measurement described above was filled in a Petri dish, and the compression measurement was performed twice in accordance with the procedures described above. The cohesiveness and adhesiveness were calculated, based on the obtained texture curve. Further, the fracture stress, adhesiveness, and cohesiveness at the time that the food composition was masticated 5 times or 20 times were also measured as described above. Regarding mastication at this time, the food composition was first hollowed out using a stainless-steel cylinder having a diameter of 40 mm, and then sliced to form a cylindrical sample having a height of 10 mm. The obtained sample was placed in the oral cavity in one bite, and disgorged after 5 or 20 mastications (each are free mastications) into a Petri dish having a diameter of 40 mm and a height of 15 mm (a container shown in the Syousyoku hyo No. 277). Then, the fracture stress, adhesiveness, and cohesiveness were measured as described above. The mastication was performed by three healthy individuals in their thirties to fifties (2 males and 1 female), and each of the obtained values was averaged.

2. Results

In terms of the food composition of Example 1, which had components stated above and a fracture stress of 36,900 N/m², syneresis was not substantially observed, and the fracture stress was thus a desired value. This indicates that the composition initially achieved a reduced risk of aspiration and had a desired fracture stress, i.e., a desired hardness, and that the composition was therefore suitable for mastication training, was easily swallowed, and achieved a reduction in aspiration.

The food composition of Example 1 had an adhesiveness and cohesiveness at the initial stage of 1,559 J/m³ and 0.49, respectively. Therefore, the composition also had desired adhesiveness and cohesiveness values. Further, the fracture stress, adhesiveness, and cohesiveness after the obtained food composition was masticated 5 times were 5,245 N/m², 392 J/m³, and 0.54, respectively, which were all desired values. Additionally, the fracture stress, adhesiveness, and cohesiveness after the obtained food composition was masticated 20 times were 1,373 N/m², 295 J/m³, and 0.75, respectively, which were also all desired values.

The above clarifies that the food composition of Example 1 was initially suitable for mastication training, and further for mastication and swallowing training. The composition was easily swallowed, achieved a reduction in aspiration, and had desired adhesiveness and cohesiveness values at the initial stage, as well as desired fracture stress, adhesiveness, and cohesiveness values after 5 mastications and 20 mastications. Additionally, in the composition, syneresis was inhibited even after 5 or more mastications. These facts indicate the following: although the composition was immediately softened after several mastications to be easily swallowed, the composition did not become overly soft after being masticated over the usual number of mastication times; therefore, the composition was highly suitable for mastication training, and further for mastication and swallowing training. The above facts also indicate the following: the composition was less likely to adhere or stick to the oral cavity and the pharynx, and had a property of satisfactorily cohering to form a bolus; further, composition remaining in the oral cavity and the pharynx, as well as the risk of aspiration, were further reduced; and the composition was easily swallowed, making it possible to more safely conduct mastication training, and further mastication and swallowing training.

Examples 2 to 19 and Comparative Examples 1 to 8

The food compositions of Examples 2 to 19 were produced in accordance with the procedures described below. Further, the compositions of Comparative Examples 1 to 8 were produced in accordance with the procedures described below. In terms of the food compositions of Examples 2 to 19 and the compositions of Comparative Examples 1 to 8, the fracture stress, adhesiveness, cohesiveness, and/or syneresis rate at the initial stage, at 5 mastications, and 20 mastications were measured as in Example 1. The elasticity was also measured with respect to some of the food compositions.

Example 2: Food Composition

The following components were used:
a crosslinked starch (the same as that used in Example 1) as a starch; xanthan gum (the same as that used in Example 1), carrageenan (the same as that used in Example 1), and gellan gum (1.5% gel, the hardness at 10° C.: 400 to 800 g/cm²) as a gelling agent; a sesame paste (the same as that used in Example 1) as an oil-containing plant paste; water; and salt (the same as that used in Example 1).

About 600 g of water was placed in a stainless-steel tank, and a mixer was started, as in Example 1. A mixture of 83 g of crosslinked starch, 1 g of xanthan gum, 9.62 g of carrageenan, and 1 g of gellan gum was gradually introduced into the tank so as not to form lumps. This operation was performed while the rotation number of the mixer was adjusted to maintain the flow of water. After the mixture was uniformly dispersed, 91 g of sesame paste was gradually introduced thereto to obtain a further uniform dispersion. After dispersion, 1 g of salt was introduced thereto, and the volume was made up to 1,000 g with about 213 g of water, followed by further stirring until a uniform dispersion was obtained. Then, 200 g each of the obtained mixture was placed into a retort pouch to obtain a composition. The thus-obtained composition was subjected to retort sterilization as described above, and a food composition (Example 2) was thereby obtained. The total amount of the starch and the gelling agent contained in this composition was about 1 by weight, based on the amount of the sesame paste. This composition had a fracture stress at the initial stage of 34,460 N/m$^2$, and the syneresis rate was 0%.

Example 3: Food Composition

About 600 g of water was placed in a stainless steel tank, and a mixer was started, as in Example 2. Each of the following components was then uniformly dispersed, as in Example 2:
78.2 g of crosslinked starch (the same as that used in Example 1) as a starch; 1.2 g of xanthan gum (the same as that used in Example 1), 10.87 g of carrageenan (the same as that used in Example 1), and 3.534 g of gellan gum (the same as that used in Example 2) as a gelling agent; 85.977 g of sesame paste (the same as that used in Example 1) as an oil-containing plant paste; and 5.01 g of salt (the same as that used in Example 1). The volume thereof was made up to 1,000 g with about 213 g of water, followed by further stirring until a uniform dispersion was obtained. Thereafter, 200 g each of the obtained mixture was placed into a retort pouch to obtain a composition. The obtained food composition was named Example 3. The total amount of the starch and the gelling agent contained in this composition was about 1.1 by weight, based on the amount of the sesame paste. This composition had a fracture stress at the initial stage of 37,210 N/m$^2$, and the syneresis rate was 0%.

Example 4: Food Composition

About 600 g of water was placed in a stainless-steel tank, and a mixer was started, as in Example 2. Each of the following components was then uniformly dispersed, as in Example 2:
78.3 g of crosslinked starch (the same as that used in Example 1) as a starch; 1.5 g of xanthan gum (the same as that used in Example 1), 9.08 g of carrageenan (the same as that used in Example 1), and 2.95 g of gellan gum (the same as that used in Example 2) as a gelling agent; 86.13 g of sesame paste (the same as that used in Example 1) as an oil-containing plant paste; and 5.02 g of salt (the same as that used in Example 1). The volume thereof was made up to 1,000 g with about 214 g of water, followed by further stirring until a uniform dispersion was obtained. Thereafter, 200 g each of the obtained mixture was placed into a retort pouch to obtain a composition. The obtained food composition was named Example 4. The total amount of the starch and the gelling agent contained in this composition was about 1.1 by weight, based on the amount of the sesame paste. This composition had a fracture stress at the initial stage of 31,150 N/m$^2$, and the syneresis rate was 0%.

Example 5: Food Composition

About 600 g of water was placed in a stainless-steel tank, and a mixer was started, as in Example 2. Each of the following components was then uniformly dispersed, as in Example 2:
78 g of crosslinked starch (the same as that used in Example 1) as a starch; 1 g of xanthan gum (the same as that used in Example 1), 10.91 g of carrageenan (the same as that used in Example 1), and 4 g of gellan gum (the same as that used in Example 2) as a gelling agent; 86 g of sesame paste (the same as that used in Example 1) as an oil-containing plant paste; and 5 g of salt (the same as that used in Example 1). The volume thereof was made up to 1,000 g with about 215 g of water, followed by further stirring until a uniform dispersion was obtained. Thereafter, 200 g each of the obtained mixture was placed into a retort pouch to obtain a composition. The obtained food composition was named Example 5. The total amount of the starch and the gelling agent contained in this composition was about 1.1 by weight, based on the amount of the sesame paste. This composition had a fracture stress at the initial stage of 44,050 N/m$^2$, and the syneresis rate was 0%.

Example 6: Food Composition

The following components were used:
78 g of crosslinked starch (the same as that used in Example 1) as a starch; 1 g of xanthan gum (the same as that used in Example 1), 10.87 g of carrageenan (the same as that used in Example 1), 4 g of gellan gum (the same as that used in Example 2), and 10 g of soybean protein (trade name: Purorina 900, produced by Fuji Oil Co., Ltd.), as a gelling agent; 97 g of sesame paste (the same as that used in Example 1) as an oil-containing plant paste; about 794 g of water; and 5 g of salt (the same as that used in Example 1).

After about 600 g of water was placed in a stainless-steel tank, a mixer was started, and a mixture of the crosslinked starch, xanthan gum, carrageenan, gellan gum, and soybean protein was gradually introduced into the tank so as not to form lumps, as in Example 1. This operation was performed while the rotation number of the mixer was adjusted to maintain the flow of water. After the mixture was uniformly dispersed, the sesame paste was gradually introduced thereto to obtain a further uniform dispersion. After dispersion, the salt was introduced thereto, and the volume was made up to 1,000 g with about 194 g of water, followed by further stirring until a uniform dispersion was obtained. Then, 200 g each of the obtained mixture was placed into a retort pouch to obtain a composition. The thus-obtained composition was subjected to retort sterilization as described above, and a food composition (Example 6) was thereby obtained. The total amount of the starch and the gelling agent contained in this composition was about 1.1 by weight, based on the amount of the sesame paste. This composition had a fracture stress at the initial stage of 46,320 N/m$^2$, and the syneresis rate was 0%.

Example 7: Food Composition

About 600 g of water was placed in a stainless-steel tank, and a mixer was started, as in Example 2. Each of the following components was then uniformly dispersed as in Example 2:

79 g of crosslinked starch (the same as that used in Example 1) as a starch; 1 g of xanthan gum (the same as that used in Example 1), 9.11 g of carrageenan (the same as that used in Example 1), and 3 g of gellan gum (the same as that used in Example 2) as a gelling agent; 86 g of sesame paste (the same as that used in Example 1) as an oil-containing plant paste; and 5 g of salt (the same as that used in Example 1). The volume thereof was made up to 1,000 g with about 217 g of water, followed by further stirring until a uniform dispersion was obtained. Thereafter, 200 g each of the obtained mixture was placed into a retort pouch to obtain a composition. The obtained food composition was named Example 7. The total amount of the starch and the gelling agent contained in this composition was about 1.1 by weight, based on the amount of the sesame paste. This composition had a fracture stress at the initial stage of 31,000 N/m$^2$, and the syneresis rate was 0%.

Example 8: Food Composition

The following components were used:
75.8 g of crosslinked starch (the same as that used in Example 1) as a starch; 0.2 g of xanthan gum (the same as that used in Example 1), 7.03 g of carrageenan (the same as that used in Example 1), and 1.85 g of gellan gum (the same as that used in Example 2) as a gelling agent; 83.4 g of sesame paste (the same as that used in Example 1) as an oil-containing plant paste; 720 g of water; 3.8 g of salt (the same as that used in Example 1); 34 g of salad oil (produced by The Nisshin OilliO Group, Ltd.); 37 g of xylitol (produced by Mitsubishi Corporation); and 37 g of brown sugar molasses (produced by Kato Brothers Honey Co. Ltd.).

After about 600 g of water was placed in a stainless-steel tank, a mixer was started, and a mixture of the crosslinked starch, xanthan gum, carrageenan, gellan gum, and xylitol was gradually introduced into the tank so as not to form lumps, as in Example 1. This operation was performed while the rotation number of the mixer was adjusted to maintain the flow of water. After the mixture was uniformly dispersed, the sesame paste and brown sugar molasses were gradually introduced thereto to achieve uniform dispersion. After dispersion, salt was added, and the volume thereof was made up to 1,000 g with about 120 g of water, followed by further stirring until a uniform dispersion was obtained. Then, 200 g each of the obtained mixture was placed into a retort pouch to obtain a composition. The thus-obtained composition was subjected to retort sterilization as described above, and a food composition (Example 8) was thereby obtained. The total amount of the starch and the gelling agent contained in this composition was about 1.0 by weight, based on the amount of the sesame paste. This composition had a fracture stress at the initial stage of 40,210 N/m$^2$, achieved a syneresis rate of 0%, and had an elasticity of 1.1.

The elasticity of the food composition was measured in accordance with the following procedures using a creep meter (RE2-33005, produced by Yamaden, Co., Ltd.) at a room temperature (20±2° C.). Specifically, the obtained food composition was placed in a refrigerator at 2 to 6° C. at least for 12 hours, and was then left to stand in a thermostatic room at 20±2° C. for 30 minutes. Thereafter, a metal Petri dish having a diameter of 40 mm and a height of 15 mm was filled with the food composition to a height of 15 mm, and compression measurement was performed once using a cylinder plunger having a diameter of 20 mm at a compression rate of 50%, a compression speed of 1 mm/sec, and at a room temperature (20±2° C.). The elasticity was calculated based on the ratio of the midpoint (absolute distortion: 50%) with respect to the midpoint 1 (absolute distortion: 25%) of the obtained compressive stress curve. The distortion was defined as absolute distortion based on the sample thickness—compression distance.

Example 9: Food Composition

About 600 g of water was placed in a stainless-steel tank, and a mixer was started, as in Example 1. Each of the following components was then uniformly dispersed, as in Example 1:
85 g of crosslinked starch (the same as that used in Example 1) as a starch; 1 g of xanthan gum (the same as that used in Example 1) and 9.88 g of carrageenan (the same as that used in Example 1) as a gelling agent; 94 g of sesame paste (the same as that used in Example 1) as an oil-containing plant paste; and 1 g of salt (the same as that used in Example 1). The volume thereof was made up to 1,000 g with about 209 g of water, followed by further stirring until a uniform dispersion was obtained. Thereafter, 200 g each of the obtained mixture was placed into a retort pouch to obtain a composition. The obtained food composition was named Example 9. The weight ratio of the total amount of the starch and the gelling agent contained in this food composition with respect to the sesame paste was about 1. This composition had a fracture stress at the initial stage of 32,150 N/m$^2$, and the syneresis rate was 0%.

Example 10: Food Composition

About 600 g of water was placed in a stainless-steel tank, and a mixer was started, as in Example 2. Each of the following components was then uniformly dispersed as in Example 2:
79 g of crosslinked starch (the same as that used in Example 1) as a starch; 9.13 g of carrageenan (the same as that used in Example 1) and 3 g of gellan gum (the same as that used in Example 2) as a gelling agent; 87 g of sesame paste (the same as that used in Example 1) as an oil-containing plant paste; and 4 g of salt (the same as that used in Example 1). The volume thereof was then made up to 1,000 g with about 219 g of water, followed by further stirring until a uniform dispersion was obtained. Thereafter, 200 g each of the obtained mixture was placed into a retort pouch to obtain a composition. The obtained food composition was named Example 10. The total amount of the starch and the gelling agent contained in this composition was about 1 by weight, based on the amount of the sesame paste. This composition had a fracture stress at the initial stage of 28,410 N/m$^2$, and the syneresis rate was 0%.

Example 11: Food Composition

The following components were used:
75 g of crosslinked starch (the same as that used in Example 1) as a starch; 1 g of xanthan gum (the same as that used in Example 1), 9 g of carrageenan (the same as that used in Example 1), and 3 g of gellan gum (the same as that used in Example 2) as a gelling agent; 82 g of sesame paste (the same as that used in Example 1) as an oil-containing plant paste; 774 g of water; 4 g of salt (the same as that used in Example 1); 35 g of plant oil (trade name: rapeseed oil, produced by The Nisshin OilliO Group, Ltd.); 11 g of extract (SANLIKE chicken consommé, produced by San-Ei Gen F.F.I., Inc.); and 6 g of flavor (trade name: sesame flavor, produced by Givaudan Japan K.K.).

After about 600 g of water was placed in a stainless-steel tank, a mixer was started, and a mixture of the crosslinked starch, xanthan gum, carrageenan, and gellan gum was then gradually introduced into the tank so as not to form lumps, as in Example 1. This operation was performed while the rotation number of the mixer was adjusted to maintain the flow of water. After the mixture was uniformly dispersed, the sesame paste and plant oil were gradually introduced thereto to achieve uniform dispersion. After dispersion, the salt, extract, and flavor were added thereto, and the volume thereof was made up to 1,000 g with about 174 g of water, followed by further stirring until a uniform dispersion was obtained. Then, 200 g each of the obtained mixture was placed into a retort pouch to obtain a composition. The thus-obtained composition was subjected to retort sterilization (F015 or more) as described above, and a food composition (Example 11) was thereby obtained. The total amount of the starch and the gelling agent contained in this composition was about 1.1 by weight, based on the amount of the sesame paste. This composition had a fracture stress at the initial stage of 29,280 N/m$^2$, achieved a syneresis rate of 0%, and had an elasticity of 1.2.

Example 12: Food Composition

The following components were used:
acetylated distarch phosphate (produced by Shikishima Starch Mfg. Co., Ltd.; degree of crosslinking: high; aging resistance: yes) as a starch; xanthan gum, (the same as that used in Example 1), carrageenan (κ type, the jelly strength at 1.5% (10° C., cylinder plunger): 400 to 800 g/cm$^2$) and gellan gum (the jelly strength at 0.3% (lactic acid Ca 0.1%) (10° C., cylinder plunger): 10 to 80 g/cm$^2$) as a gelling agent; a chocolate paste (trade name: Sonton chocolate spread (water content: 2%), produced by Sonton Food Industry Co., Ltd.) as an oil-containing paste; water; and granulated sugar.

About 600 g of water was placed in a stainless-steel tank, and a mixer was started, as in Example 1. Then, a mixture of 82 g of modified starch, 28 g of granulated sugar, 1 g of xanthan gum, 7.6 g of carrageenan, and 2 g of gellan gum was gradually introduced into the tank so as not to form lumps. This operation was performed while the rotation number of the mixer was adjusted to maintain the flow of water. After the mixture was uniformly dispersed, 90 g of chocolate paste was gradually introduced thereto to obtain a further uniform dispersion. After dispersion, the volume thereof was made up to 1,000 g with water, followed by further stirring until a uniform dispersion was obtained. Then, the obtained composition was introduced into a plastic cup (height: 165 mm) to fill it to the maximum (50 g). The thus-obtained composition was subjected to retort sterilization (128° C., 7 minutes), and a food composition (Example 12) was thereby obtained. The total amount of the starch and the gelling agent contained in this composition was about 1 by weight, based on the amount of the chocolate paste. This composition had a fracture stress at the initial stage of 25,270 N/m$^2$, and the syneresis rate was 0%.

Example 13: Food Composition

The following components were used:
a modified starch (the same as that used in Example 12) as a starch; xanthan gum (the same as that used in Example 1), carrageenan (κ type, the jelly strength at 1.5% (10° C., cylinder plunger): 400 to 800 g/cm$^2$), and gellan gum (the jelly strength at 0.3% (lactic acid Ca 0.1%) (10° C., cylinder plunger): 10 to 80 g/cm$^2$) as a gelling agent; a condensed milk paste (trade name: Morinaga Milk sweetened condensed milk (water content: 28%), produced by Morinaga Milk Industry Co., Ltd.) as an oil-containing paste; water; and granulated sugar.

About 600 g of water was placed in a stainless-steel tank, and a mixer was started as in Example 1. Then, a mixture of 82 g of modified starch, 28 g of granulated sugar, 1 g of xanthan gum, 7.6 g of carrageenan, and 2 g of gellan gum was gradually introduced into the tank so as not to form lumps. This operation was performed while the rotation number of the mixer was adjusted to maintain the flow of water. After the mixture was uniformly dispersed, 90 g of condensed milk paste was gradually introduced thereto to obtain a further uniform dispersion. After dispersion, the volume thereof was made up to 1,000 g with water, followed by further stirring until a uniform dispersion was obtained. Then, the obtained composition was introduced into a plastic cup (height: 165 mm) to fill it to the maximum (50 g). The thus-obtained composition was subjected to retort sterilization (128° C., 7 minutes), and a food composition (Example 13) was thereby obtained. The total amount of the starch and the gelling agent contained in this composition was about 1 by weight, based on the amount of the condensed milk paste. This composition had a fracture stress at the initial stage of 30,300 N/m$^2$, and the syneresis rate was 0%.

Example 14: Food Composition

The following components were used:
a modified starch (the same as that used in Example 12) as a starch; xanthan gum (the same as that used in Example 1), carrageenan (κ type, the jelly strength at 1.5% (10° C., cylinder plunger): 400 to 800 g/cm$^2$), and gellan gum (the jelly strength at 0.3% (lactic acid Ca 0.1%) (10° C., cylinder plunger): 10 to 80 g/cm$^2$) as a gelling agent; a milk paste (trade name: Meiji milk cream (water content: 1.7%), produced by Meiji Co., Ltd.) as an oil-containing paste; water; and granulated sugar.

About 600 g of water was placed in a stainless-steel tank, and a mixer was started, as in Example 1. Then, a mixture of 86 g of modified starch, 28 g of granulated sugar, 1 g of xanthan gum, 8 g of carrageenan, and 2.1 g of gellan gum was gradually introduced into the tank so as not to form lumps. This operation was performed while the rotation number of the mixer was adjusted to maintain the flow of water. After the mixture was uniformly dispersed, 90 g of milk paste was gradually introduced thereto to obtain a further uniform dispersion. After dispersion, the volume thereof was made up to 1,000 g with water, followed by further stirring until a uniform dispersion was obtained. Then, the obtained composition was introduced into a plastic cup (height: 165 mm) to fill it to the maximum (50 g). The thus-obtained composition was subjected to retort sterilization (128° C., 7 minutes), and a food composition (Example 14) was thereby obtained. The total amount of the starch and the gelling agent contained in this composition was about 1.1 by weight, based on the amount of the milk paste. This composition had a fracture stress at the initial stage of 25,940 N/m$^2$, and the syneresis rate was 0%.

Example 15: Food Composition

The following components were used:
a modified starch (the same as that used in Example 12) as a starch; xanthan gum (the same as that used in Example 1), carrageenan (κ type, the jelly strength at 1.5% (10° C., cylinder plunger): 400 to 800 g/cm$^2$), and gellan gum (the jelly strength at 0.3% (lactic acid Ca 0.1%) (10° C., cylinder plunger): 10 to 80 g/cm$^2$) as a gelling agent; a chocolate paste (a company-produced chocolate paste for fondue) as an oil-containing paste; water; and granulated sugar.

About 600 g of water was placed in a stainless-steel tank, and a mixer was started, as in Example 1. Then, a mixture of 83 g of modified starch, 28 g of granulated sugar, 1 g of xanthan gum, 8.4 g of carrageenan, and 2.2 g of gellan gum was gradually introduced into the tank so as not to form lumps. This operation was performed while the rotation number of the mixer was adjusted to maintain the flow of water. After the mixture was uniformly dispersed, 90 g of chocolate paste was gradually introduced thereto to obtain a further uniform dispersion. After dispersion, the volume thereof was made up to 1000 g with water, followed by further stirring until a uniform dispersion was obtained. Then, the obtained composition was introduced into a plastic cup (height: 165 mm) to fill it to the maximum (50 g). The thus-obtained composition was subjected to retort sterilization (128° C., 7 minutes), and a food composition (Example 15) was thereby obtained. The total amount of the starch and the gelling agent contained in this composition was about 1.1 by weight, based on the amount of the chocolate paste. This composition had a fracture stress at the initial stage of 28,580 N/m$^2$, and the syneresis rate was 0%.

Example 16: Food Composition

The following components were used:
a modified starch (the same as that used in Example 12) as a starch; xanthan gum (the same as that used in Example 1), carrageenan (κ type, the jelly strength at 1.5% (10° C., cylinder plunger): 400 to 800 g/cm$^2$), and gellan gum (the jelly strength at 0.3% (lactic acid Ca 0.1%) (10° C., cylinder plunger): 10 to 80 g/cm$^2$) as a gelling agent; a cream paste (trade name: Takanashi pure fresh cream (water content: 88%), produced by Takanashi Milk Products Co., Ltd.) as an oil-containing paste; water; and granulated sugar.

About 600 g of water was placed in a stainless-steel tank, and a mixer was started, as in Example 1. Then, a mixture of 81 g of modified starch, 28 g of granulated sugar, 0.2 g of xanthan gum, 7.1 g of carrageenan, and 2 g of gellan gum was gradually introduced into the tank so as not to form lumps. This operation was performed while the rotation number of the mixer was adjusted to maintain the flow of water. After the mixture was uniformly dispersed, 89 g of cream paste was gradually introduced thereto to obtain a further uniform dispersion. After dispersion, the volume thereof was made up to 1,000 g with water, followed by further stirring until a uniform dispersion was obtained. Then, the obtained composition was introduced into a plastic cup (height: 165 mm) to fill it to the maximum (50 g). The thus-obtained composition was subjected to retort sterilization (128° C., 7 minutes), and a food composition (Example 16) was thereby obtained. The total amount of the starch and the gelling agent contained in this composition was about 1 by weight, based on the amount of the cream paste. This composition had a fracture stress at the initial stage of 27,850 N/m$^2$, and the syneresis rate was 0%.

Example 17: Food Composition

The following components were used:
a modified starch (the same as that used in Example 12) as a starch; xanthan gum (the same as that used in Example 1), carrageenan (κ type, the jelly strength at 1.5% (10° C., cylinder plunger): 400 to 800 g/cm$^2$), and gellan gum (the jelly strength at 0.3% (lactic acid Ca 0.1%) (10° C., cylinder plunger): 10 to 80 g/cm$^2$) as a gelling agent; a white paste (trade name: white sauce (water content: 51%), produced by Heinz Japan Ltd.) as an oil-containing paste; salt; and water.

About 600 g of water was placed in a stainless-steel tank, and a mixer was started, as in Example 1. Then, a mixture of 81 g of modified starch, 0.2 g of xanthan gum, 7.1 g of carrageenan, and 2 g of gellan gum was gradually introduced into the tank so as not to form lumps. This operation was performed while the rotation number of the mixer was adjusted to maintain the flow of water. After the mixture was uniformly dispersed, a mixture of 160 g of white paste and 36.4 g of oil was gradually introduced thereto to obtain a further uniform dispersion. After dispersion, 1 g of salt was introduced thereto, and the volume thereof was made up to 1000 g with water, followed by further stirring until a uniform dispersion was obtained. Then, the obtained composition was introduced into a plastic cup (height: 165 mm) to fill it to the maximum (50 g). The thus-obtained composition was subjected to retort sterilization (128° C., 7 minutes), and a food composition (Example 17) was thereby obtained. The total amount of the starch and the gelling agent contained in this composition was about 1 by weight, based on the amount of the white paste. This composition had a fracture stress at the initial stage of 25,850 N/m$^2$, and the syneresis rate was 0%.

Example 18: Food Composition

The following components were used:
a crosslinked starch (the same as that used in Example 1) as a starch; xanthan gum (the same as that used in Example 1), carrageenan (the same as that used in Example 1), and gellan gum (the same as that used in Example 2) as a gelling agent; a sesame paste (the same as that used in Example 1) as an oil-containing plant paste; water; salt (the same as that used in Example 1); a plant oil (the same as that used in Example 11); an extract (the same as that used in Example 11); and a flavor (the same as that used in Example 11).

About 100 g of water was placed in a stainless-steel tank, and a stirrer was started. Then, a mixture of 3 g of crosslinked starch and 1 g of xanthan gum was gradually introduced into the tank so as not to form lumps. This operation was performed while the stirring speed of the stirrer was adjusted to maintain the flow of water to obtain a uniform dispersion (considered as A). Separately, 500 g of water was placed into a stainless-steel tank, and the stirrer was started. After 4 g of salt, 11 g of extract, and A above were added thereto, a mixture of 73 g of crosslinked starch, 9 g of carrageenan, and 3 g of gellan gum was gradually introduced into the tank so as not to form lumps. This operation was also performed while the stirring speed of the stirrer was adjusted to maintain the flow of water. After the mixture was uniformly dispersed, a mixture of 82 g of sesame paste and 35 g of plant oil was gradually added thereto to obtain a further uniform dispersion. After dispersion, the volume was made up to 1,000 g with 6 g of flavor and water, and the resulting product was further uniformly stirred with a mixer until the viscosity became 1,500 mPa·s or more. Then, the obtained composition was introduced into a plastic cup (height: 165 mm) to fill it to the maximum (50 g). The thus-obtained composition was subjected to retort sterilization (121° C., 4 minutes), and a food composition (Example 18) was thereby obtained. The total amount of the starch and the gelling agent contained in this composition was about 1.1 by weight, based on the amount of the sesame paste. This composition had a fracture stress at the initial stage of 58,474 N/m², and the syneresis rate was 0%.

Example 19: Food Composition

The following components were used:
a modified starch (the same as that used in Example 1) as a starch; xanthan gum (the same as that used in Example 1), carrageenan (κ type, the jelly strength at 1.5% (10° C., cylinder plunger): 400 to 800 g/cm²), and gellan gum (the jelly strength at 0.3% (lactic acid Ca 0.1%) (10° C., cylinder plunger): 10 to 80 g/cm²) as a gelling agent; a sesame paste (the same as that used in Example 1) as an oil-containing paste; sugar (produced by the Hokuren Federation of Agricultural Cooperatives); xylitol (produced by Mitsubishi Shoji Foodtech Co., Ltd.); salt (the same as that used in Example 1); flavor (made by Takasago International Corp.); and water.

About 100 g of water was placed in a stainless-steel tank, and a stirrer was started. Then, a mixture of 3 g of granulated sugar and 0.5 g of xanthan gum was gradually introduced into the tank so as not to form lumps. This operation was performed while the stirring speed of the stirrer was adjusted to maintain the flow of water to obtain a uniform dispersion (considered as A). Separately, 500 g of water was placed into a stainless-steel tank, and the stirrer was started. After 3.8 g of salt and A above were added thereto, a mixture of 90 g of modified starch, 8.2 g of carrageenan, and 0.7 g of gellan gum was gradually introduced into the tank so as not to form lumps. This operation was also performed while the stirring speed of the stirrer was adjusted to maintain the flow of water. After the mixture was uniformly dispersed, a mixture of 89 g of sesame paste was gradually introduced thereto to obtain a further uniform dispersion. After dispersion, the volume was made up to 1,000 g with 3.7 g of xylitol, 5 g of flavor, and water, and the resulting product was further uniformly stirred with a mixer until the viscosity became 1,500 mPa·s or more. Then, the obtained composition was introduced into a plastic cup (height: 165 mm) to fill it to the maximum (50 g). The thus-obtained composition was subjected to retort sterilization (121° C., 4 minutes), and a food composition was thereby obtained. The total amount of the starch and the gelling agent contained in this composition was about 1.1 by weight, based on the amount of the sesame paste. This composition had a fracture stress at the initial stage of 65,431 N/m², and the syneresis rate was 0%.

Comparative Example 1

The following components were used:
100.7 g of crosslinked starch (hydroxypropyl distarch phosphate, degree of crosslinking: low) as a starch; 1 g of xanthan gum (the same as that used in Example 1) and 9.3 g of carrageenan (the same as that used in Example 1) as a gelling agent; 110.7 g of sesame paste (the same as that used in Example 1) as an oil-containing plant paste; 734 g of water; and 44.3 g of plant oil (trade name: rapeseed oil, produced by The Nisshin OilliO Group, Ltd.).

About 600 g of water was placed in a stainless-steel tank, and a mixer was started, as in Example 1. Thereafter, a mixture of the crosslinked starch, xanthan gum, and carrageenan was gradually introduced into the tank so as not to form lumps. This operation was performed while the rotation number of the mixer was adjusted to maintain the flow of water. After the mixture was uniformly dispersed, the sesame paste and plant oil were gradually introduced thereto to achieve uniform dispersion. The volume thereof was then made up to 1,000 g with about 134 g of water, followed by further stirring until a uniform dispersion was obtained. Then, 200 g each of the obtained mixture was placed into a retort pouch and subjected to retort sterilization (F015 or more) as described above, and a composition (Comparative Example 1) was thereby produced. The total amount of the starch and the gelling agent contained in this composition was about 1 by weight, based on the amount of the sesame paste. The fracture stress at the initial stage was unmeasurable.

Comparative Example 2

The following components were used:
178.61 g of crosslinked starch (hydroxypropyl distarch phosphate, degree of crosslinking: low) as a starch; 1.74 g of xanthan gum (the same as that used in Example 1) and 21.78 g of carrageenan (the same as that used in Example 1) as a gelling agent; 196.47 g of sesame paste (the same as that used in Example 1) as an oil-containing plant paste; 522.76 g of water; and 78.63 g of plant oil (trade name: rapeseed oil, produced by The Nisshin OilliO Group, Ltd.).

About 400 g of water was placed in a stainless steel tank, and a mixer was started, as in Example 1. Thereafter, a mixture of the crosslinked starch, xanthan gum, and carrageenan was gradually introduced into the tank so as not to form lumps. This operation was performed while the rotation number of the mixer was adjusted to maintain the flow of water. After the mixture was uniformly dispersed, the sesame paste was gradually introduced thereto to obtain a further uniform dispersion. The volume thereof was then made up to 1,000 g with about 123 g of water, followed by further stirring until a uniform dispersion was obtained. Then, 200 g each of the obtained mixture was placed into a retort pouch and subjected to retort sterilization as described above, and a composition (Comparative Example 2) was thereby produced. The total amount of the starch and the gelling agent contained in this composition was about 1 by weight, based on the amount of the sesame paste. The fracture stress at the initial stage was unmeasurable.

Comparative Example 3

The following components were used:
87 g of crosslinked starch (the same as that used in Example 1) as a starch; 1 g of crystalline cellulose preparation (the same as that used in Example 1) as a gelling agent; 87 g of sesame paste (the same as that used in Example 1) as an oil-containing plant paste; and 825 g of water.

About 600 g of water was placed in a stainless steel tank, and a mixer was started, as in Example 1. Thereafter, a mixture of the crosslinked starch and crystalline cellulose preparation was gradually introduced into the tank so as not to form lumps. This operation was performed while the rotation number of the mixer was adjusted to maintain the flow of water. After the mixture was uniformly dispersed, the sesame paste was gradually introduced thereto to obtain a further uniform dispersion. The volume thereof was then made up to 1,000 g with about 225 g of water, followed by further stirring until a uniform dispersion was obtained. Then, 225 g each of the obtained mixture was placed into a retort pouch and subjected to retort sterilization as described above, and a composition (Comparative Example 3) was thereby produced. The total amount of the starch and the gelling agent contained in this composition was about 1 by weight, based on the amount of the sesame paste. The fracture stress at the initial stage was 5,712 N/m$^2$.

Comparative Example 4

The following components were used:
a modified starch (the same as that used in Example 1) as a starch; xanthan gum (the same as that used in Example 1), carrageenan (the same as that used in Example 1), and gellan gum (the same as that used in Example 1) as a gelling agent; a sesame paste (the same as that used in Example 1) as a paste; water; a seasoning (glutamic acid Na, produced by Ajinomoto Co., Inc.; powder seasoning, produced by San-Ei Gen F.F.I., Inc.); and salt.

About 600 g of water was placed in a stainless-steel tank, and a mixer was started, as in Example 1. Thereafter, a mixture of 40 g of modified starch, 0.2 g of xanthan gum, 7.1 g of carrageenan, and 2 g of gellan gum was gradually introduced into the tank so as not to form lumps. This operation was performed while the rotation number of the mixer was adjusted to maintain the flow of water. After the mixture was uniformly dispersed, a mixture of 89 g of sesame paste and 36.4 g of oil was gradually introduced thereto to obtain a further uniform dispersion. After dispersion, 1 g of salt and 4.1 g of the seasoning were added, and the volume thereof was made up to 1,000 g with water, followed by further stirring until a uniform dispersion was obtained. Then, the obtained mixture was introduced into a plastic cup (height: 165 mm) to fill it to the maximum (50 g), and was subjected to retort sterilization (128° C., 7 minutes), and a composition (Comparative Example 4) was thereby obtained. The total amount of the starch and the gelling agent contained in this composition was about 0.55 by weight, based on the amount of the sesame paste. The fracture stress at the initial stage was 10,540 N/m$^2$ and the elasticity was 0.9%.

Comparative Example 5

The following components were used:
a modified starch (the same as that used in Example 1) as a starch; xanthan gum (the same as that used in Example 1), carrageenan (the same as that used in Example 1), and gellan gum (the same as that used in Example 1) as a gelling agent; a sesame paste (the same as that used in Example 1) as a paste; water; a seasoning (glutamic acid Na, produced by Ajinomoto Co., Inc.; powder seasoning, produced by San-Ei Gen F.F.I., Inc.); and salt.

600 g of water was placed in a stainless steel tank, and a mixer was started, as in Example 1. Thereafter, a mixture of 81 g of modified starch, 0.2 g of xanthan gum, 23.6 g of carrageenan, and 6.5 g of gellan gum was gradually introduced into the tank so as not to form lumps. This operation was performed while the rotation number of the mixer was adjusted to maintain the flow of water. After the mixture was uniformly dispersed, a mixture of 89 g of sesame paste and 36.4 g of oil was gradually introduced thereto to obtain a further uniform dispersion. After dispersion, 1 g of salt and 4.1 g of seasoning were added thereto, and the volume thereof was made up to 1,000 g with water, followed by further stirring until a uniform dispersion was obtained. Then, the obtained mixture was introduced into a plastic cup (height: 165 mm) to fill it to the maximum (50 g), and was subjected to retort sterilization (128° C., 7 minutes), and a composition (Comparative Example 5) was thereby obtained. The total amount of the starch and the gelling agent contained in this composition was about 1.25 by weight, based on the amount of the sesame paste. The fracture stress at the initial stage was unmeasurable, and the elasticity was 0.9%.

Comparative Example 6

The following components were used:
a modified starch (the same as that used in Example 1) as a starch; a sesame paste (the same as that used in Example 1) as a paste; water; a seasoning (glutamic acid Na, produced by Ajinomoto Co., Inc.; powder seasoning, produced by San-Ei Gen F.F.I., Inc.); and salt.

600 g of water was placed in a stainless-steel tank, and a mixer was started, as in Example 1. Thereafter, a mixture of 81 g of modified starch was gradually introduced into the tank so as not to form lumps. This operation was performed while the rotation number of the mixer was adjusted to maintain the flow of water. After the mixture was uniformly dispersed, a mixture of 89 g of sesame paste and 36.4 g of oil was gradually introduced thereto to obtain a further uniform dispersion. After dispersion, 1 g of salt and 4.1 g of seasoning were added thereto, and the volume thereof was made up to 1,000 g with water, followed by further stirring until a uniform dispersion was obtained. Then, the obtained mixture was introduced into a plastic cup (height: 165 mm) to fill it to the maximum (50 g), and was subjected to retort sterilization (128° C., 7 minutes), and a composition (Comparative Example 6) was thereby obtained. The total amount of the starch and the gelling agent contained in this composition was about 0.9 by weight, based on the amount of the sesame paste. The fracture stress at the initial stage was 1,942 N/m$^2$, the adhesion at the initial stage was 713 J/m$^3$, and the cohesiveness at the initial stage was 0.9. The elasticity was unmeasurable since the slope of stress was not obtained.

Comparative Example 7

The following components were used:
a modified starch (the same as that used in Example 1) as a starch; xanthan gum (the same as that used in Example 1), carrageenan (the same as that used in Example 1), and gellan gum (the same as that used in Example 1) as a gelling agent; a sesame paste (the same as that used in Example 1) as a paste; water; a seasoning (glutamic acid Na, produced by Ajinomoto Co., Inc.; powder seasoning, produced by San-Ei Gen F.F.I., Inc.); and salt.

600 g of water was placed in a stainless-steel tank, and a mixer was started, as in Example 1. Then, a mixture of 81 g of modified starch, 0.2 g of xanthan gum, 7.1 g of carrageenan, and 2 g of gellan gum was gradually introduced into the tank so as not to form lumps. This operation was performed while the rotation number of the mixer was adjusted to maintain the flow of water. After the mixture was uniformly dispersed, a mixture of 40 g of sesame paste and 36.4 g of oil was gradually introduced thereto to obtain a further uniform dispersion. After dispersion, 1 g of salt and 4.1 g of seasoning were added, and the volume thereof was made up to 1,000 g with water, followed by further stirring until a uniform dispersion was obtained. Then, the obtained mixture was introduced into a plastic cup (height: 165 mm) to fill it to the maximum (50 g), and was subjected to retort sterilization (128° C., 7 minutes), and a composition (Comparative Example 7) was thereby obtained. The total amount of the starch and the gelling agent contained in this composition was about 2.26 by weight, based on the amount of the sesame paste. The fracture stress at the initial stage was 18,650 N/m², adhesion at the initial stage was 1,374 J/m³, and cohesiveness at the initial stage was 0.5.

Comparative Example 8

The following components were used:
a modified starch (the same as that used in Example 1) as a starch; xanthan gum (the same as that used in Example 1), carrageenan (the same as that used in Example 1), and gellan gum (the same as that used in Example 1) as a gelling agent; a sesame paste (the same as that used in Example 1) as a paste; water; a seasoning (glutamic acid Na, produced by Ajinomoto Co., Inc.; powder seasoning, produced by San-Ei Gen F.F.I., Inc.); and salt.

600 g of water was placed in a stainless-steel tank, and a mixer was started, as in Example 1. Then, a mixture of 69 g of modified starch, 0.2 g of xanthan gum, 6.1 g of carrageenan, and 1.7 g of gellan gum was gradually introduced into the tank so as not to form lumps. This operation was performed while the rotation number of the mixer was adjusted to maintain the flow of water. After the mixture was uniformly dispersed, a mixture of 76 g of sesame paste and 31.1 g of oil was gradually introduced thereto to obtain a further uniform dispersion. After dispersion, 1 g of salt and 58 g of seasoning were added, and the volume thereof was made up to 1,000 g with water, followed by further stirring until a uniform dispersion was obtained. Then, the obtained mixture was introduced into a plastic cup (height: 165 mm) to fill it to the maximum (50 g), and was subjected to retort sterilization (128° C., 7 minutes), and a composition (Comparative Example 8) was thereby obtained. The total amount of the starch and the gelling agent contained in this composition was about 1 by weight, based on the amount of the sesame paste. The fracture stress at the initial stage was 3,406 N/m².

2. Results

In terms of the food composition of Example 2, which had components above and a fracture stress of 34,460 N/m², syneresis was not substantially observed, and the value of fracture stress was thus satisfactory. In terms of the food compositions of Examples 3 to 19 as well, syneresis was not substantially observed, and the values of fracture stress were thus satisfactory. This confirms that the food compositions of Examples 2 to 19 initially achieved a reduction in the risk of aspiration and had a desired fracture stress, i.e., desired hardness; thus, these food compositions were suitable for mastication training, and achieved a reduction in aspiration.

The adhesiveness and cohesiveness of the food composition of Example 2 at the initial stage were 3,825 J/m³ and 0.5, respectively. The fracture stress, adhesiveness, and cohesiveness of this composition after 5 mastications were 3,777 N/m², 248 J/m³, and 0.6, respectively. The fracture stress, adhesiveness, and cohesiveness of this composition after 20 mastications were 1,186 N/m², 317 J/m³, and 0.8, respectively.

The adhesiveness and cohesiveness of the food composition of Example 3 at the initial stage were 3,269 J/m³ and 0.5, respectively. The fracture stress, adhesiveness, and cohesiveness of this composition after 5 mastications were 6,836 N/m², 148 J/m³, and 0.5, respectively. The fracture stress, adhesiveness, and cohesiveness of this composition after 20 mastications were 1,342 N/m², 175 J/m³, and 0.7, respectively.

The adhesiveness and cohesiveness of the food composition of Example 4 at the initial stage were 1,864 J/m³ and 0.5, respectively. The fracture stress, adhesiveness, and cohesiveness of this composition after 5 mastications were 2,809 N/m², 95 J/m³, and 0.6, respectively. The fracture stress, adhesiveness, and cohesiveness of this composition after 20 mastications were 1,186 N/m², 245 J/m³, and 0.7, respectively.

The adhesiveness and cohesiveness of the food composition of Example 5 at the initial stage were 3,424 J/m³ and 0.5, respectively. The fracture stress, adhesiveness, and cohesiveness of this composition after 5 mastications were 4,495 N/m², 72 J/m³, and 0.6, respectively. The fracture stress, adhesiveness, and cohesiveness of this composition after 20 mastications were 1,842 N/m², 391 J/m³, and 0.7, respectively.

The adhesiveness and cohesiveness of the food composition of Example 6 at the initial stage were 2,667 J/m³ and 0.5, respectively. The fracture stress, adhesiveness, and cohesiveness of this composition after 5 mastications were 7,773 N/m², 123 J/m³, and 0.6, respectively. The fracture stress, adhesiveness, and cohesiveness of this composition after 20 mastications were 2,341 N/m², 279 J/m³, and 0.6, respectively.

The adhesiveness and cohesiveness of the food composition of Example 7 at the initial stage were 1,809 J/m³ and 0.5, respectively. The fracture stress, adhesiveness, and cohesiveness of this composition after 5 mastications were 4,339 N/m², 144 J/m³, and 0.6, respectively. The fracture stress, adhesiveness, and cohesiveness of this composition after 20 mastications were 1,342 N/m², 233 J/m³, and 0.7, respectively.

The adhesiveness and cohesiveness of the food composition of Example 8 at the initial stage were 2,078 J/m³ and 0.5, respectively. The fracture stress, adhesiveness, and cohesiveness of this composition after 5 mastications were 4,152 N/m², 362 J/m³, and 0.6, respectively. The fracture stress, adhesiveness, and cohesiveness of this composition after 20 mastications were 1,342 N/m², 183 J/m³, and 0.6, respectively.

The adhesiveness and cohesiveness of the food composition of Example 9 at the initial stage were 2,365 J/m³ and 0.4, respectively. The fracture stress, adhesiveness, and cohesiveness of this composition after 5 mastications were 3,715 N/m², 216 J/m³, and 0.5, respectively. The fracture stress, adhesiveness, and cohesiveness of this composition after 20 mastications were 1,592 N/m², 288 J/m³, and 0.7, respectively.

The adhesiveness and cohesiveness of the food composition of Example 10 at the initial stage were 2,198 J/m³ and 0.5, respectively. The fracture stress, adhesiveness, and cohesiveness of this composition after 5 mastications were 2,685 N/m², 268 J/m³, and 0.6, respectively. The fracture stress, adhesiveness, and cohesiveness of this composition after 20 mastications were 1,061 N/m², 279 J/m³, and 0.7, respectively.

The adhesiveness and cohesiveness of the food composition of Example 11 at the initial stage were 2,481 J/m³ and 0.5, respectively. The fracture stress, adhesiveness, and cohesiveness of this composition after 5 mastications were 3,527 N/m², 209 J/m³, and 0.6, respectively. The fracture stress, adhesiveness, and cohesiveness of this composition after 20 mastications were 1,093 N/m², 253 J/m³, and 0.7, respectively.

The adhesiveness and cohesiveness of the food composition of Example 12 at the initial stage were 804 J/m³ and 0.4, respectively. The initial elasticity was 1.8. The fracture stress, adhesiveness, and cohesiveness of this composition after 5 mastications were 7,671 N/m², 441 J/m³, and 0.4, respectively. The fracture stress, adhesiveness, and cohesiveness of this composition after 20 mastications were 2,642 N/m$^2$, 198 J/m$^3$, and 0.8, respectively.

The adhesiveness and cohesiveness of the food composition of Example 13 at the initial stage were 1,573 J/m$^3$ and 0.4, respectively. The initial elasticity was 1.1. The fracture stress, adhesiveness, and cohesiveness of this composition after 5 mastications were 5,157 N/m$^2$, 857 J/m$^3$, and 0.6, respectively. The fracture stress, adhesiveness, and cohesiveness of this composition after 20 mastications were 2,528 N/m$^2$, 336 J/m$^3$, and 0.4, respectively.

The adhesiveness and cohesiveness of the food composition of Example 14 at the initial stage were 3,870 J/m$^3$ and 0.5, respectively. The initial elasticity was 1.1. The fracture stress, adhesiveness, and cohesiveness of this composition after 5 mastications were 4,775 N/m$^2$, 95 J/m$^3$, and 0.4, respectively. The fracture stress, adhesiveness, and cohesiveness of this composition after 20 mastications were 2,005 N/m$^2$, 363 J/m$^3$, and 0.7, respectively.

The adhesiveness and cohesiveness of the food composition of Example 15 at the initial stage were 691 J/m$^3$ and 0.4, respectively. The initial elasticity was 2.2. The fracture stress, adhesiveness, and cohesiveness of this composition after 5 mastications were 6,080 N/m$^2$, 254 J/m$^3$, and 0.4, respectively. The fracture stress, adhesiveness, and cohesiveness of this composition after 20 mastications were 3,501 N/m$^2$, 373 J/m$^3$, and 0.4, respectively.

The adhesiveness and cohesiveness of the food composition of Example 16 at the initial stage were 1,038 J/m$^3$ and 0.5, respectively. The initial elasticity was 1.8. The fracture stress, adhesiveness, and cohesiveness of this composition after 5 mastications were 3,788 N/m$^2$, 109 J/m$^3$, and 0.5, respectively. The fracture stress, adhesiveness, and cohesiveness of this composition after 20 mastications were 1,942 N/m$^2$, 86 J/m$^3$, and 0.4, respectively.

The adhesiveness and cohesiveness of the food composition of Example 17 at the initial stage were 1,105 J/m$^3$ and 0.4, respectively. The initial elasticity was 1.8. The fracture stress, adhesiveness, and cohesiveness of this composition after 5 mastications were 3,501 N/m$^2$, 270 J/m$^3$, and 0.5, respectively. The fracture stress, adhesiveness, and cohesiveness of this composition after 20 mastications were 1,369 N/m$^2$, 266 J/m$^3$, and 0.6, respectively.

The adhesiveness and cohesiveness of the food composition of Example 18 at the initial stage were 2,843 J/m$^3$ and 0.5, respectively. The initial elasticity was 1.9. The fracture stress, adhesiveness, and cohesiveness of this composition after 5 mastications were 5,952 N/m$^2$, 204 J/m$^3$, and 0.5, respectively. The fracture stress, adhesiveness, and cohesiveness of this composition after 20 mastications were 3,310 N/m$^2$, 377 J/m$^3$, and 0.5, respectively.

The adhesiveness and cohesiveness of the food composition of Example 19 at the initial stage were 2,215 J/m$^3$ and 0.5, respectively. The initial elasticity was 1.4. The fracture stress, adhesiveness, and cohesiveness of this composition after 5 mastications were 8,053 N/m$^2$, 270 J/m$^3$, and 0.5, respectively. The fracture stress, adhesiveness, and cohesiveness of this composition after 20 mastications were 3,438 N/m$^2$, 194 J/m$^3$, and 0.4, respectively.

The above results clarify that the food compositions of Examples 2 to 19 were initially suitable for mastication training, and further for mastication and swallowing training; were easily swallowed; achieved a reduction in aspiration; and also had desired values of adhesiveness and cohesiveness at the initial stage, as well as desired values of fracture stress, adhesiveness, and cohesiveness after 5 and 20 mastications. In these food compositions, the syneresis was inhibited even after 5 or more mastications. This indicates the following: although these compositions were immediately softened to be easily swallowed after several mastications, the compositions did not become overly soft after being masticated over the usual number of mastication times; therefore, the compositions were highly suitable for mastication training, and further mastication and swallowing training. The above also indicates the following: the adherence and stickiness of these compositions in the oral cavity and the pharynx are reduced, the compositions had a property of satisfactorily cohering to form a bolus; the residual of the compositions in the oral cavity and the pharynx, as well as the risk of aspiration, were also further reduced; and the compositions were easily swallowed, and were highly suitable for mastication training, and further mastication and swallowing training.

In contrast, in terms of the composition of Comparative Example 1, not only the fracture stress but also the adhesiveness and cohesiveness were unmeasurable at the initial stage. Further, the fracture stress, adhesiveness, and cohesiveness of this composition after 5 mastications were 10,890 N/m$^2$, 37 J/m$^3$, and 0.6, respectively, and the fracture stress, adhesiveness, and cohesiveness after 20 mastications were 2,778 N/m$^2$, 318 J/m$^3$, and 0.6, respectively. Therefore, the hardness of the composition of Comparative Example 1 was not suitable, at least, for mastication training. The adhesiveness and cohesiveness were also not satisfactory.

In terms of the composition of Comparative Example 2 as well, the fracture stress, adhesiveness, and cohesiveness at the initial stage were unmeasurable. Further, the fracture stress, adhesiveness, and cohesiveness of this composition after 5 mastications were 31,310 N/m$^2$, 38 J/m$^3$, and 0.6, respectively, and the fracture stress, adhesiveness, and cohesiveness after 20 mastications were 11,520 N/m$^2$, 295 J/m$^3$, and 0.5, respectively. Therefore, the hardness of the composition of Comparative Example 2 was also not suitable, at least, for mastication training. The adhesiveness and cohesiveness were also not satisfactory.

The composition of Comparative Example 3 had a fracture stress, adhesiveness, and cohesiveness at the initial stage of 5,712 N/m$^2$, 834 J/m$^3$, and 0.5, respectively. Therefore, the hardness of the composition of Comparative Example 3 was also not suitable, at least, for mastication training.

The composition of Comparative Example 4 had a fracture stress at the initial stage of 10,540 N/m$^2$. Therefore, the hardness of the composition of Comparative Example 4 was also not suitable, at least, for mastication training.

The fracture stress of the composition of Comparative Example 5 at the initial stage was unmeasurable, and the hardness of this composition was thus not suitable, at least, for mastication training.

The composition of Comparative Example 6 had a fracture stress, adhesiveness, and cohesiveness at the initial stage of 1,942 N/m$^2$, 713 J/m$^3$, and 0.9, respectively. Therefore, the hardness of the composition of Comparative Example 3 was also not suitable, at least, for mastication training.

The composition of Comparative Example 7 had a fracture stress of 18,650 N/m$^2$, an adhesion of 1,374 J/m$^3$, and a cohesiveness of 0.5, at the initial stage. Therefore, at least any one of the fracture stress, adhesiveness, and cohesiveness was not satisfactory.

The composition of Comparative Example 8 had a fracture stress of 3,406 N/m$^2$ at the initial stage, and the hardness of this compound was not suitable, at least, for mastication training.

The invention claimed is:

1. A food composition containing (i) a starch, (ii) a gelling agent, (iii) a paste, and (iv) water,
   the amount of the water contained in the composition being 65 wt % or more and less than 90 wt %,
   a ratio of the total amount of the starch and the gelling agent being about 1 or more by weight, based on the amount of the paste,
   the total amount of the starch, the gelling agent, the paste, and the water being 85 to 100 wt %,
   the composition having a syneresis rate of 0 to 3%,
   the composition having a fracture stress of 20,000 to 70,000 N/m$^2$,
   the fracture stress being measured by filling a metal Petri dish having a diameter of 40 mm and a height of 15 mm with the food composition to a height of 15 mm, and performing compression measurement twice using a cylinder plunger having a diameter of 20 mm with a clearance of 5 mm at a compression speed of 10 mm/sec, and at a room temperature (20±2° C.), and
   the composition contains the starch in an amount of 5 to 10 wt %, the gelling agent in an amount of 0.5 to 3 wt %, and the paste in an amount of 5 to 20 wt %.

2. The food composition according to claim 1, wherein the composition has an adhesiveness of 4,000 J/m$^3$ or less.

3. The food composition according to claim 1, wherein the paste contains an oil, carbohydrate, and a protein, the paste being an emulsified paste in which an oil, carbohydrate, and protein are combined without being separated.

4. The food composition according to claim 1, wherein the total amount of the starch and the gelling agent is 1 to 2.2 by weight, based on the amount of the paste.

5. The food composition according to claim 1, wherein the paste is at least one member selected from the group consisting of plant pastes and pastes made from animal-derived materials.

6. The food composition according to claim 1, wherein the gelling agent is at least one member selected from the group consisting of κ carrageenan and gellan gum.

7. The food composition according to claim 1, wherein the composition has a fracture stress of 1,000 to 5,000 N/m$^2$ after 20 mastications.

8. The food composition according to claim 1, wherein the composition has a fracture stress of 1,000 to 10,000 N/m$^2$ after 5 mastications.

9. The food composition according to claim 1, wherein the composition has an adhesiveness of 500 J/m$^3$ or less after 20 mastications.

10. The food composition according to claim 1, wherein the composition has an adhesiveness of 1,000 J/m$^3$ or less after 5 mastications.

11. The food composition according to claim 1, wherein the composition has a cohesiveness of 0.4 to 0.8.

12. The food composition according to claim 1, wherein the composition has a cohesiveness of 0.4 to 0.8 after 20 mastications.

13. The food composition according to claim 1, wherein the composition has a cohesiveness of 0.4 to 0.8 after 5 mastications.

14. The food composition according to claim 1, wherein the composition is retort-sterilized.

* * * * *